June 26, 1956 J. D. BROWNELL Plant Pat. 1,491
ROSE PLANT
Filed Aug. 3, 1955
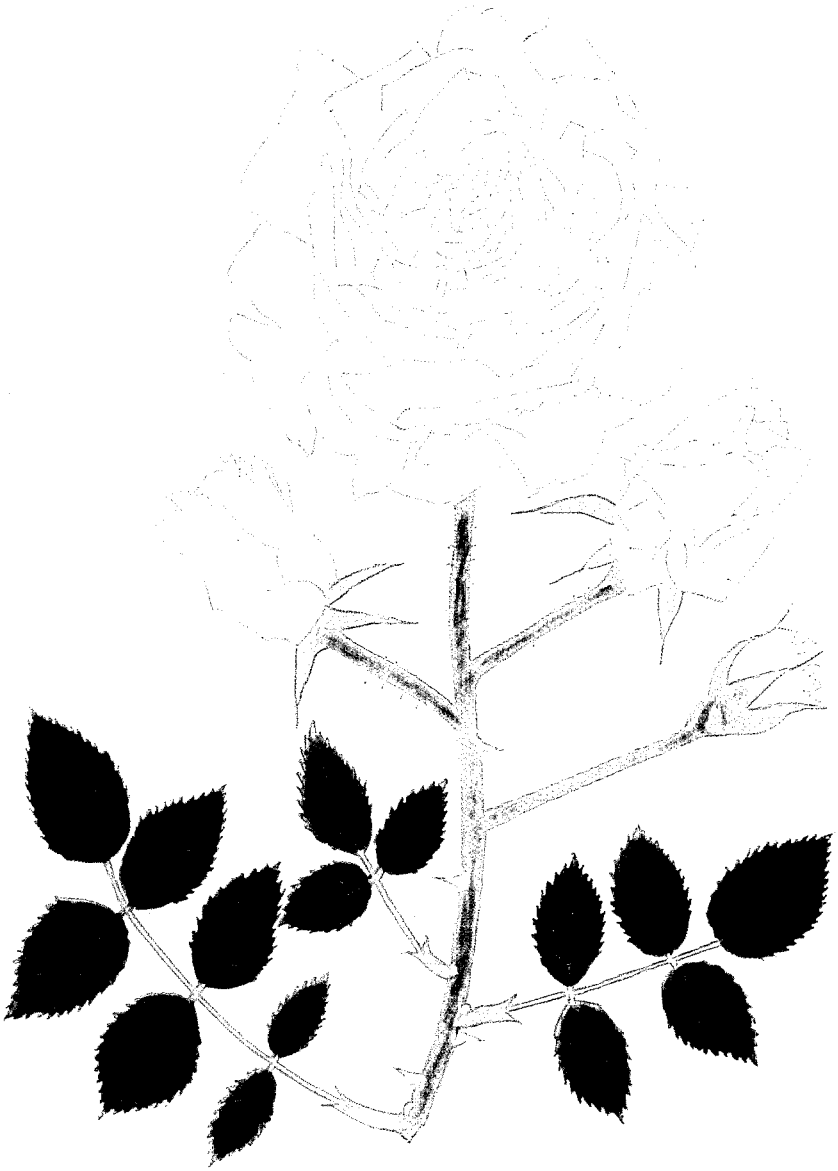
INVENTOR.
Josephine D. Brownell.

United States Patent Office

Plant Pat. 1,491

Patented June 26, 1956

1,491

ROSE PLANT

Josephine D. Brownell, Little Compton, R. I.

Application August 3, 1955, Serial No. 526,342

1 Claim. (Cl. 47—61)

My invention or discovery relates to a rose plant and especially to a new, original and distinct variety of the class known commercially as "hybrid teas" and also is a variant in that class, newly called Grandiflora, being a *Rosa wichuraiana* hybrid tea hybrid, discovered by me and under my direction in the breeding grounds of my research gardens in Little Compton, Rhode Island, which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States;

The yellow color (ordinary dictionary definition) of its petals, in combination with the unique brilliance thereof and their tendency to hold this color under exposure, and the informal arrangement of the petals.

The notable resistance to blackspot;

The novelty and variation within certain definite limits of the form of the bloom, its character of holding that form for a long time and the petallage of the flowers;

Its character of fragrance;

Its unusual abundance of flowers, at bloom time and after early bloom time and until frost;

The intensity of its remontant and everblooming or reblooming character.

Its character of ascending in height by recurrent branching and progressively longer stems from the base.

The character of producing many seven leafleted leaves, which character seldom has obtained on hybrid teas not having *Rosa wichuraiana* ancestry, but frequently obtains on flower stems of descendants of *Rosa wichuraiana* of the dwarf reblooming type;

And especially its characteristic of freedom from premature defoliation by blackspot, under certain definite conditions of exposure, without any cultural control.

In the accompanying drawing forming a part of this specification I have shown my new rose in its natural colors, that is, as near as is possible to do so artificially.

The color of my new rose is yellow and later softens to lighter shades, especially on the outer edges of the petals.

ESSENTIAL INFORMATION

*Type*

Hybrid tea, *Rosa wichuraiana* hybrid, dwarf for garden display, cut flower and forcing or growing under glass.

*Class*

Hybrid tea crossed with *Rosa wichuraiana* hybrid, further restricted by originator to include only those varieties that can survive moderately low sub-zero temperatures.

*Breeding*

It came into being as a seedling of the following varieties, the pollen parent was "V for Victory" Plant Patent No. 543 and the seed parent was produced by crossing a sport of "New Dawn" Plant Patent No. 27 with a sport of "Copper Glow" Plant Patent No. 458, descendant from *Rosa wichuraiana,* discovered by me and by my assistant and co-worker, among my hybridized seedlings on August 17, 1950 [1], growing in my field at Little Compton, Rhode Island.

I have since made and directed extensive propagations and tests of this variety and flower.

Plants of this variety budded from the stem grown on this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1952 and 1953 inclusive and the characters have successively reproduced, true to the original seedling.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three or more on each stem, in the usual hybrid tea type of cluster. The pedicels and peduncles are medium in diameter and medium in length, erect, stiff, nearly smooth, except for a few fine hairs. Stems are long, diameter medium and notably stiff and rigid, with prickles normal in quantity.

*Quantity of bloom*

Free, being cumulative in quantity from year to year as the plant increases in size, flowering through the summer.

*Fragrance*

Distinctive and pronounced, pleasing China tea in combination with that of *Rosa wichuraiana,* under favorable environment.

*Bud*

Neck normal as described, opens well, being little to not at all affected by hot or wet weather or both, as to color and form, except at very high temperatures the color is less intense and the form of the petals is less recurled.

Before the calyx breaks the size is medium, form moderately pointed, infrequently with one or more sepals having small foliaceous parts extending beyond the apex of the calyx up to about one-quarter inch, the number and size of the foliaceous parts being variable, otherwise the sepals are usually normal and regular, tapering to lanceolate at their apex, turning back nearly perpendicular to the pedicel as the bud opens.

Color of bud as calyx opens, Buttercup Yellow at 5/3; color reference to English Horticultural Color Chart. [2]

*Bloom*

As the bud opens and the flower develops to maturity the color starts as above and slowly softens to Indian Yellow at 6/2 and later, especially at the tips, to 6/1. This color description applies to both sides of the petals.

The flower usually varies when well grown in size from four to five inches in diameter when fully open, petals average between 35 and 50, frequently some smaller petals and petaloids in the center, variable in number.

The flower opens high centered, moderately informal,

[1] This and other dates herein are approximate.

[2] Color references to same unless otherwise indicated.

slightly recurled, with late display of stamens and pistils. The petals are variable from obovate to ovate. Texture is medium to thick both sides brilliant. The time of opening in favorable conditions is four to six days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Reproductive organs*

Stamens, quantity variable, of slightly uneven length.

Anthers, Burnt Orange o14/3. Filaments, nearly Maize Yellow at 607/1.

Pistils are several of slightly uneven lengths, averaging about one-half inch long.

Ovaries are usually all inclosed.

Hips frequently develop to ovoid to globular, color comparable with that of leaves with variable colored overlay on the side exposed to the sun, moderately smooth; walls, thin, fleshy, medium in size.

Sepals are persistent and break off cleanly.

PLANT

*Foliage*

Is abundant, of compound leaves of three to five leaflets near the flower, five leaflets lower down the stems and frequently seven leaflets in the middle of the stem and nearer the base. Size of leaflets medium, averaging in size about half way between the average hybrid tea and the *Rosa wichuraiana* leaflets. The leaflets as shown are drawn to scale two-thirds as compared to that of the flowers.

Form of leaflets usually ovate with apex moderately acute, base rounded, margins with pointed serrations, petiolules short.

The leaflets average in width about two-thirds of their length.

Color references hereinafter are to Robert Ridgway Color Standard.

Color of leaflets on the upper surface is slightly variable from Dark Dull Yellow Green, with reverse side nearly Asphodel Green.

The rachises are medium, moderately narrow to slender, upper side smooth except some very short hairs on edges. Under side moderately smooth, usually 3 to 5 short prickles.

Stipules are medium, averaging about three-quarters of an inch long, with sharp points medium in length, the upper edges of which normally form an angle of about 90 degrees.

Habit, dwarf, upright, compact, due to constitutional factors inherited from *Rosa wichuraiana*; more cumulative in growth from year to year than the normal hybrid tea rose plant, averaging in height when well grown four to four and one-half feet. The growth is moderately free at first, developing more rapidly after one or two years.

Color of mature stems is slightly more reddish than the upper surface of mature leaves, shading variously lighter.

Prickles, several, frequently two to four between leaves, averaging in length about one-quarter inch, of nearly Crimson color, turning lighter throughout and later to nearly colorless; in form, sharp pointed. (The description nearly Crimson and slightly more reddish in the above paragraph are ordinary dictionary definitions.)

WINTER RESISTANCE

A notable characteristic of this new rose is the resistance to moderate sub-zero temperatures in combination with its hybrid tea character and its *Rosa wichuraiana* ancestry. This variety with grafted bud and plant above that bud entirely exposed above ground to moderate sub-zero temperatures survived and bloomed normally the following season. (The word temperature refers to the Fahrenheit scale.)

COMPARISONS

The rose variety most nearly similar to my new rose is probably the variety "V for Victory" Plant Patent No. 543, they differ in that the variety "V for Victory" does not grow as tall as my new rose. The color does not hold as well in sunshine, it does not send canes or stems from the base as frequently as does my new rose and its floral form is more formal in petal arrangement.

I claim:

A new and distinct variety of rose plant, substantially as shown and described characterized by its color pattern, fragrance, form and color and its Wichuraiana traits.

No references cited.